United States Patent
Luong et al.

[11] Patent Number: 5,997,615
[45] Date of Patent: Dec. 7, 1999

[54] LARGE-SAMPLE ACCESSORY FOR A GAS CHROMATOGRAPH

[76] Inventors: Huan V. Luong, P.O. Box 81601, Fairbanks, Ak. 99708; Hsing Kuang Lin, 2143 Bridgewater Dr., Fairbanks, Ak. 99709; Howard Fruwirth, P.O. Box 73994, Fairbanks, Ak. 99707; George S. Mueller, 4204 York Ave., Fairbanks, Ak. 99709

[21] Appl. No.: 09/103,107

[22] Filed: Jun. 23, 1998

[51] Int. Cl.⁶ .................................................. B01D 15/08
[52] U.S. Cl. ............................................. 96/105; 96/106
[58] Field of Search .................... 95/87, 89; 96/101–106

[56] References Cited

U.S. PATENT DOCUMENTS

| | | | |
|---|---|---|---|
| 4,162,977 | 7/1979 | Guillemin et al. | 96/105 X |
| 4,422,860 | 12/1983 | Feinstein | 96/105 X |
| 4,477,266 | 10/1984 | Yang et al. | 95/89 X |
| 4,559,063 | 12/1985 | Munari et al. | 95/89 X |
| 4,805,441 | 2/1989 | Sides et al. | 95/87 X |
| 5,522,988 | 6/1996 | Cortes et al. | 96/104 X |
| 5,545,252 | 8/1996 | Hinshaw et al. | 96/102 X |
| 5,588,988 | 12/1996 | Gerstel et al. | 96/101 |
| 5,596,876 | 1/1997 | Manura et al. | 95/87 X |
| 5,711,786 | 1/1998 | Hinshaw | 96/102 X |
| 5,714,677 | 2/1998 | Parsy et al. | 95/89 X |
| 5,779,765 | 7/1998 | Grob et al. | 96/105 X |
| 5,803,951 | 9/1998 | Wada et al. | 96/102 X |
| 5,837,353 | 10/1998 | O'Neil | 96/101 |

OTHER PUBLICATIONS

Gerstel Large Volumer in Sampleer Brochur pp. 5–7 Date Unknown.

Ultra–trace GC and GC/MS Fully Automatic Computer Controlled Instruments with Enhanced Cpabilities for Trace Analysis Through Cold On Column Large Volume Sample Injection, P. Magni et al., Reprint of Paer Presented at 18th International Symposium on Capillary Chromatography, Riva del Garda (Italy) May 2–24, 1996.

*Primary Examiner*—Robert Spitzer
*Attorney, Agent, or Firm*—R. Russel Austin

[57] ABSTRACT

A gas chromatograph includes a heating enclosure, an injection port extending through a wall of the enclosure, a capillary column within the heating enclosure and connected at a distal end thereof to a detector. The injection port is arranged to accept a carrier gas for gaseous components an analyte solution through the capillary column to the detector. An expansion chamber is located within the heating enclosure between the injection port and the capillary column. The expansion chamber is arranged such that it provides fluid communication between the injection port and the capillary column. First and second conduits are attached to the expansion chamber in fluid communication therewith. The first conduit is arranged to accept the carrier gas from outside the heating enclosure and the second conduit is arranged to vent excess vapor from the chamber to a point outside the heating enclosure.

9 Claims, 5 Drawing Sheets

LARGE-SAMPLE ACCESSORY FOR A GAS CHROMATOGRAPH

TECHNICAL FIELD OF THE INVENTION

The present invention relates generally to gas chromatography. The invention relates in particular to an accessory device for a gas chromatograph which permits analysis of large volume samples thereby.

BACKGROUND OF THE INVENTION

A gas chromatograph (GC) is a powerful instrument for analyzing chemicals, particularly organic chemicals. This instrument, when coupled with a mass spectrometer or other specific detectors, is considered the analytical instrument of choice in many laboratories around the world.

All advanced GC systems currently commercially available are equipped with capillary columns. Over the last 30 years, addition of the capillary column has increased the power of this instrument. Previously, all GC were equipped with packed columns. These columns have inside diameter as large as 4 mm, and are only a few meters long, for example about ten meters long. To improve the separation power of the GC, instrument makers replaced the packed columns with capillary columns. These columns are much smaller in diameter than the original packed columns, for example with an inside diameter of about 0.3 mm, but may be as long as one-hundred meters.

With this capillary type of column, chemists have the power to separate closely related compounds, thus, greatly increasing their ability to identify and quantify chemicals. However, the capillary column has one significant drawback in that it is unable to accept large sample volume.

By way of illustration, during the introduction (injection) of a sample into a conventional GC via an injection port lined by an inlet sleeve, the sample is vaporized in the injection port, which greatly increases the volume of the sample. For the solvent hexane, for example, a typical injection of 1 microliter ($\mu l$) will have an expanded volume of about 200.0 $\mu l$. A 5.0 $\mu l$ injection will have an expansion volume of almost 1000 $\mu l$ In a conventional GC, the largest inlet sleeve lining an injection port has a maximum volume of about 942 microliters. As all expanded sample gases have to enter the capillary column, the capillary column is flooded if a sample volume greater than 5.0 $\mu l$ is injected. The large expansion volume also leads to an increase in the pressure inside the injection port. This can lead to problems such as backflash and sleeve breakage.

The above-discussed drawback thus limits to few microliters the sample size which can be usefully injected into a conventional GC equipped with capillary column. Several GC manufacturers offer optional replacement injection systems to allow somewhat larger sample injections. Such replacement systems may increase the sample size capability only by about 250 $\mu l$ and the original injection system must be removed to accommodate the replacement. Accordingly, the cost of the optional equipment and the labor cost of replacement may be sufficiently high that such a replacement does not provide a cost effective way to improve an existing system.

There is a need for an "add-on" device that can be attached to an existing injecting system of a conventional GC, and allows for larger sample injection. Preferably such a device would allow the injection volume of a conventional capillary-column GC to be increased from a few microliters to over one milliliter. Increasing the injection volume to over one milliliter could improve the detection power of a conventional GC over 1000 times (depending on how large a volume is injected).

SUMMARY OF THE INVENTION

In one aspect of the present invention, above discussed shortcomings of prior-art gas chromatograph apparatus are addressed in gas chromatograph apparatus comprising a heating enclosure, and an injection port extending through a wall of the enclosure. A proximal end of the injection port is located outside the heating enclosure and arranged to accept an injected solution of an analyte. The injection port extends into the heating enclosure a distance sufficient to form an expansion chamber located within the heating enclosure for expanding the analyte solution into solvent vapor and gaseous analyte components. A capillary column is located within the heating enclosure for dynamically separating the gaseous analyte components. The capillary column is attached at a proximal end thereof to the expansion chamber in fluid communication therewith, and at the distal end thereof to a detector for detecting the gaseous analyte components. First and second conduits are attached to the expansion chamber in fluid communication therewith through a wall thereof. The first conduit, which is attached to the expansion chamber nearest the distal end thereof, is arranged to accept the carrier gas from outside the heating enclosure. The second conduit, which is attached to the expansion chamber between the proximal end thereof and the attachment point thereon of the first conduit, is arranged to vent excess solvent vapor from the expansion chamber to a point outside the heating enclosure.

In another aspect of the present invention shortcomings of prior art gas chromatograph apparatus are addressed by accessory apparatus for attachment to such prior-art gas chromatograph apparatus. The prior art gas chromatograph apparatus includes a heating enclosure, an injection port extending through a wall of the enclosure and arranged to accept an injected solution of an analyte, a capillary column within the heating enclosure, the capillary column normally in fluid connection at a proximal end thereof with the injection port for receiving gaseous analyte components and, at a distal end thereof, to a detector. The injection port is arranged to accept a carrier gas, the carrier gas is for driving the gaseous components of the analyte through the capillary column to the detector. The accessory apparatus of the present invention comprises an expansion chamber attachable between the injection port and the capillary column, the chamber is for expanding the analyte solution into solvent vapor and the gaseous analyte components. The expansion chamber has a proximal end attachable to the injection port, or insertable through the injection port, and a distal end attachable to the capillary column at the proximal end thereof such that the chamber is located inside the heating enclosure and provides fluid communication between the injection port and the capillary column when attached therebetween. First and second conduits are attached to the chamber in fluid communication therewith through a wall thereof. The first conduit, which is attached to the expansion chamber nearest the distal end thereof, is arranged to accept the carrier gas from outside the heating enclosure. The second conduit, which is attached to the expansion chamber between the proximal end thereof and the attachment point thereon of the first conduit, is arranged to vent solvent vapor from the chamber.

In one experiment, gas chromatograph apparatus modified by such accessory apparatus was able to accept and analyze a sample nine-hundred times greater in volume than the unmodifed apparatus would accept and analyze. Through use of the larger sample in the modified apparatus it was possible to detect and analyze, with an accuracy of within about 2%, polychlorinated biphenyls (PCB) in a concentration of as low as 10 parts per million. This concentration was not detectable at all using the small sample volume of the unmodified apparatus.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

Figure 1:
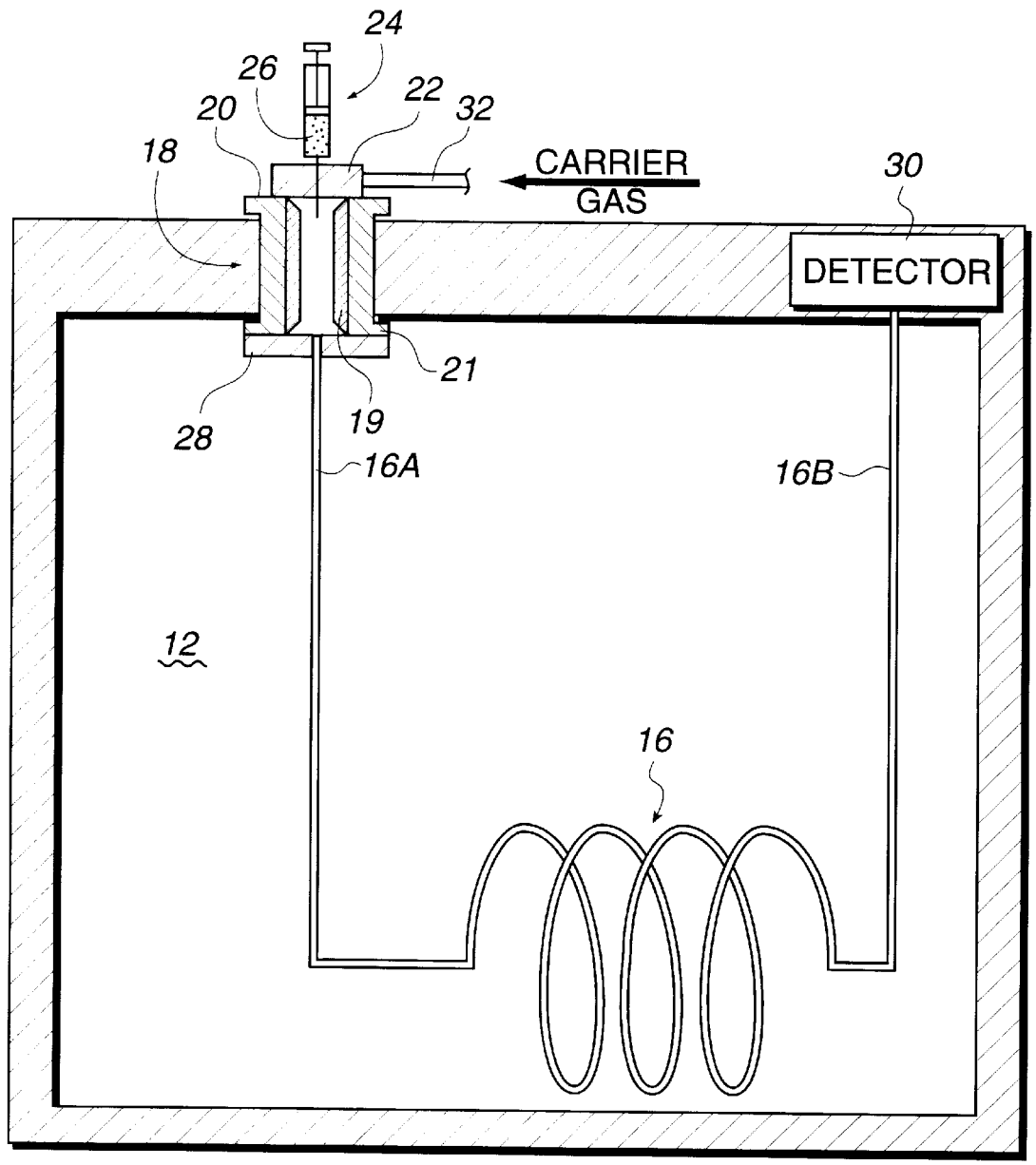
FIG. 1 is a general cross-section view schematically illustrating prior art gas chromatograph apparatus including a heating enclosure, an injection port extending through a wall of the heating enclosure, a capillary column within the heating enclosure and attached at one end thereof to the injection port and at the other end thereof to a detector.

Turning now to the drawings, wherein like components are illustrated by like reference numerals FIG. 1 schematically depicts a prior art gas chromatograph (GC) 10. GC 10 includes a heatable enclosure 12 surrounded by an enclosure wall 14. Within heatable enclosure 12 is a capillary column 16 which is typically in the form of a coil about 100 meters (m) in length. Column 16 is shown in FIG. 1 as a single line to emphasize the capillary nature of the column. Those skilled in the art to which the present invention pertains will recognize, of course that a capillary bore (not shown) typically having a diameter of about 0.3 mm extends completely through the column. An injection port 18 extends through wall 14 of enclosure 12. Injection port 18 is lined by a removable inlet sleeve 19. On the top (proximal end) 20 of injection port 18 is mounted an injection adaptor 22 which is arranged to accommodate an injection syringe 24 or the like which contains, in solution 26, a sample to be analyzed (analyte). Proximal end 16A of capillary column 16 is attached to distal end 21 of injection port 18, in fluid communication therewith, via an adaptor 28. Distal end 16B of capillary column 16 is attached to and in fluid communication with a detector 30. Detector 30, for example, may be an electron capture detector (ECD),a flame ionization detector (FID), a mass spectrometer detector (MS) or the like. Attached to injection adaptor 22 and in fluid communication therewith is a conduit 32 for admitting a carrier gas into the injection port.

Briefly, when sample 26 is injected into injection port 18, it vaporizes into solvent vapor and gaseous analyte components. Injected carrier gas drives gaseous analyte components and solvent vapor through capillary column 16 to detector 30. The gaseous analyte components arrive and sequentially at the detector generally in order of increasing mass.

Figure 2:
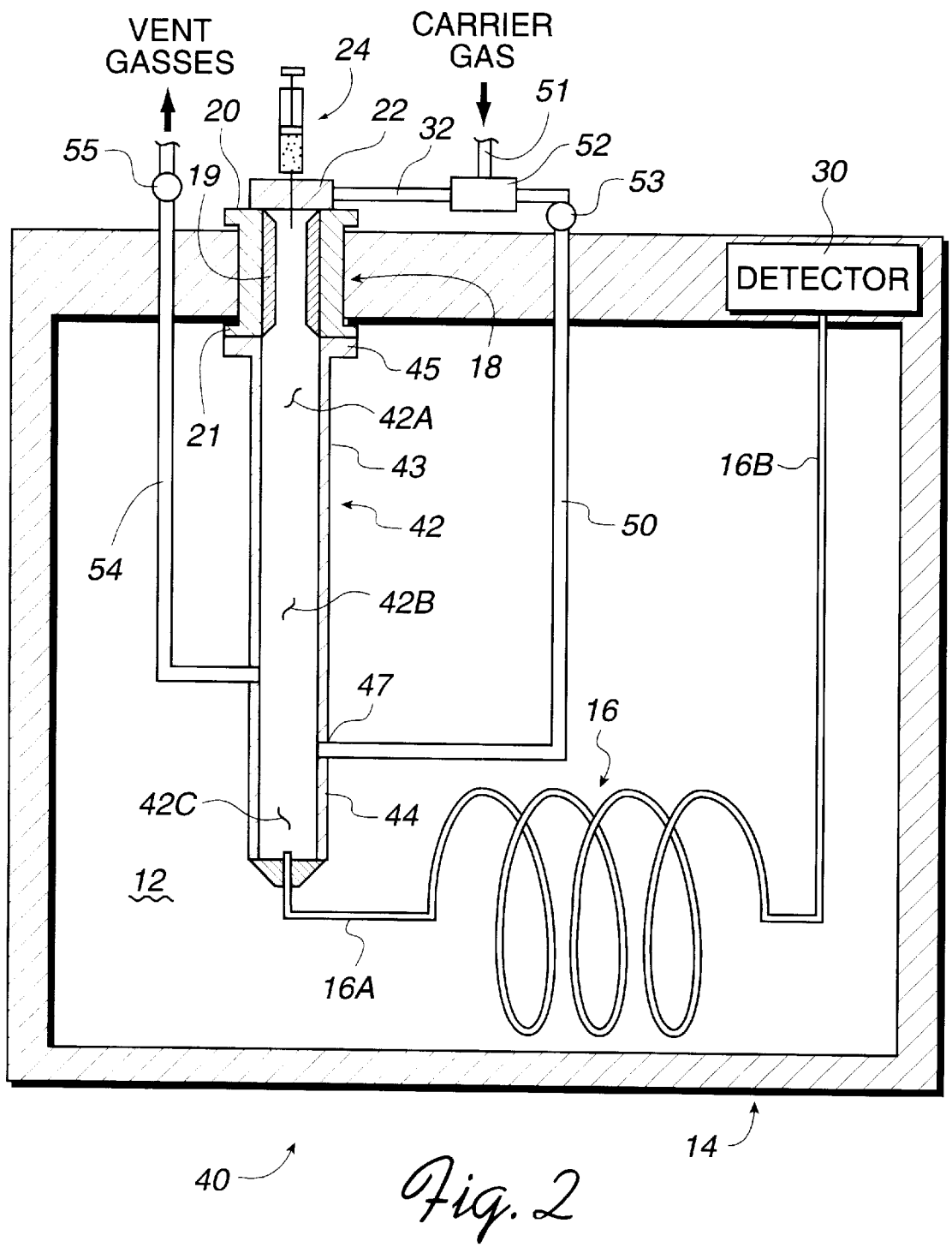
FIG. 2 is a general cross-section view schematically illustrating one preferred embodiment of a gas chromatograph apparatus in accordance with the present invention, including a heating enclosure, an injection port extending through a wall of the heating enclosure, an expansion chamber within the heating enclosure and attached to the injection port, and a capillary column attached at one end thereof to the expansion chamber and at the other end thereof to a detector.

Referring now to FIG. 2, a preferred embodiment 40 of a gas chromatograph in accordance with the present invention is depicted. Here GC 10 of FIG. 1 has been modified by adding an expansion chamber 42, located entirely in heatable enclosure 12, between injection port 18 and capillary column 16. Proximal end 43 of expansion chamber 42 is attached via a flange 45 to distal end 21 of injection port 18 in fluid communication therewith. Distal end 44 of expansion chamber 42 is attached to and in fluid communication with proximal end 16A of capillary column 16. Distal end 16B of capillary column 16 is attached to and in fluid communication with detector 30 as in GC 10.

Preferably, expansion chamber 42 is cylindrical and has an inside diameter about the same as that of injection port 18, typically on the order of about 1 centimeter. The volume of expansion chamber 42 has preferably at least twice, and most preferably at least four times the volume of inlet sleeve 19, i.e., a volume preferably greater than 2000 $\mu$l and most preferably greater than about 4000 $\mu$l.

Carrier gas is delivered to the lower portion of expansion chamber 42 via a conduit 50 in fluid communication therewith, as well as via injection port 18 as discussed above. Conduits 50 and 32 are connected to a common carrier gas source via conduit 51, a "T" junction 52 and a valve 53. A vent conduit 54 is attached to and in fluid communication with expansion chamber 42 between proximal end 43 thereof and the point 47 thereon at which conduit 50 is attached. Vent conduit 54 has a valve 55 outside of enclosure 12.

Figure 3:
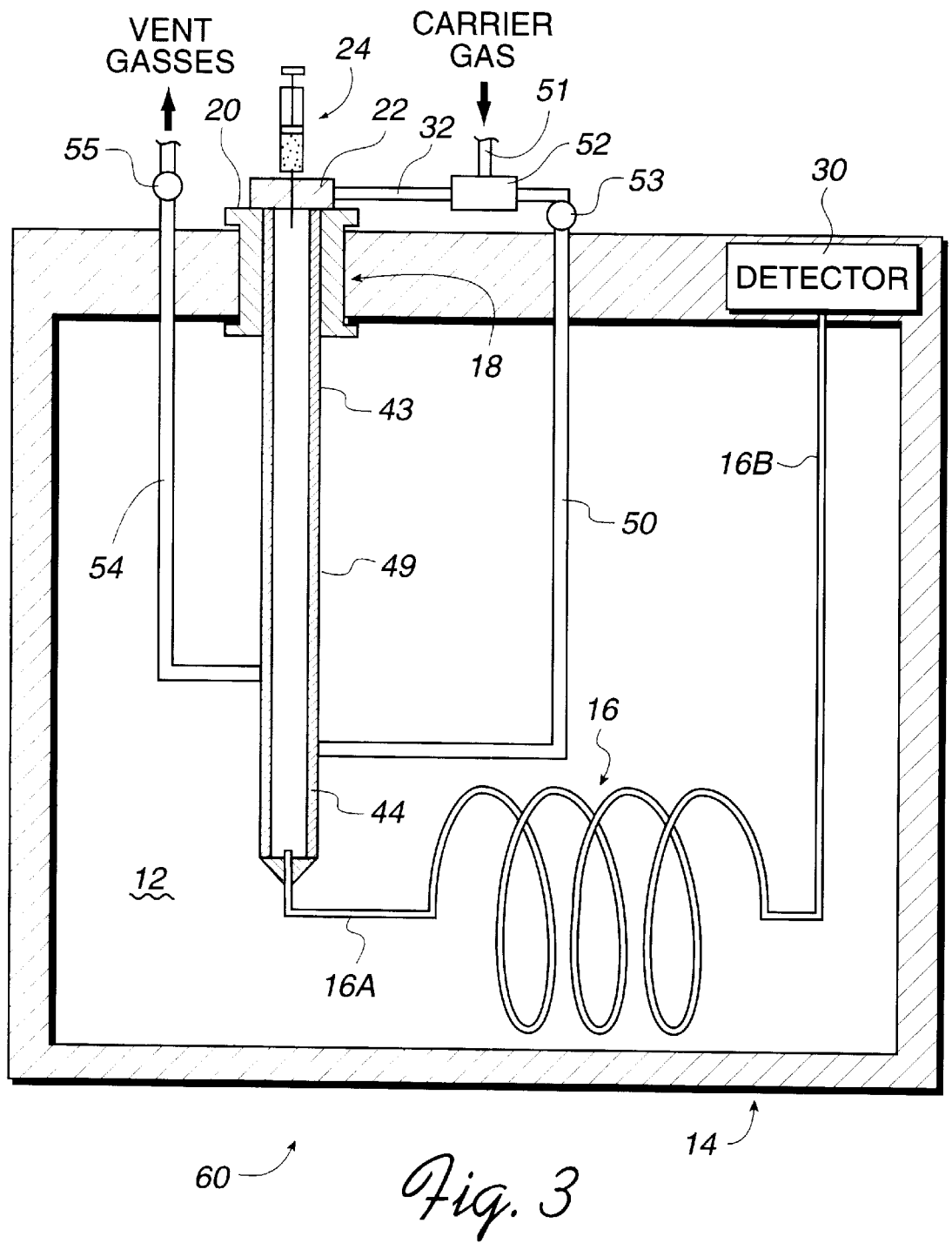
FIG. 3 is a general cross-section view schematically illustrating another preferred embodiment of a gas chromatograph apparatus in accordance with the present invention, including a heating enclosure, an injection port extending through a wall of the heating enclosure, a sleeve extending through the injection port into the heating enclosure, thereby forming an expansion chamber within the heating enclosure, and a capillary column within the heating enclosure and attached at one end thereof to the expansion chamber and at the other end thereof to a detector.

Referring to FIG. 3, another embodiment 60 of a gas chromatograph in accordance with the present invention is illustrated. GC 60 is similar in most respects to GC 40 with the exception that expansion chamber 42 of GC 40 is replaced with an expansion chamber 49 which extends through injection port 18 in the manner of an extended liner or sleeve. Injection liner 19 must be removed from injection port 18 before expansion chamber 49 is extended therethrough.

The arrangements of GCs 40 and 60 are accessory modifications of a prior-art GC which can be simply and inexpensively made while retaining the original injection apparatus of the prior-art GC.

Referring again to FIG. 2, expansion chamber 42 can be considered as having three functional regions. A first (upper) region 42A closest injection port 18 allows gas expansion beyond the injection port. A second (mid) region 42B provides a ventilation system, allowing excess solvent resulting from a large sample injection to be released away from expansion chamber 42 via conduit 54. A third (lower), region 42C below vent conduit 54, provides additional carrier gas flow into the system. This is most important in a gas chromatograph in accordance with the present invention as it functions to divide expanded analyte gases from excess solvent vapor in the expansion chamber as well as to remove this excess solvent vapor from the chamber. This excess solvent vapor would otherwise "flood" the apparatus.

It should be noted here that while for most existing apparatus expansion chamber 42 will be most usefully cylindrical, it may be of any other convenient shape. Important is that the expansion chamber should have at least the same volume of original injection port 18, and preferably should have about four or more times that volume.

One preferred method of using apparatus 40 or apparatus 60 is as follows. First the temperature of enclosure 12 is set at a relatively low value, for example about 100° C., sufficient to vaporize solvent in preference to the heavier analyte when the sample is injected into the expansion chamber. Valve 53 is open to allow carrier gas to admitted via conduit 50 and valve 55 is opened to allow escape of excess solvent vapor. Valve 53 preferably allows regulation of carrier gas flow through conduit 50 according to the sample volume. After a period of about five to twenty minutes, valve 55 is closed and the temperature of enclosure 12 is raised to a higher temperature, sufficient to vaporize analyte. Valve 53 may remain open during this operation. From this point, operation of the apparatus takes place as it would with conventional GC apparatus, with the advantage however that the ratio of analyte gases to solvent vapor is one or more orders of magnitude greater than would be the case in such conventional apparatus due to the above described pre-expansion and separation of excess solvent. This advantage can be appreciated from a description of tests of apparatus in accordance with the present invention set forth below.

One set of tests of a gas chromatograph in accordance with the present invention was performed using polychlorinated biphenyl (PCB) as an analyte. The analysis was performed using, first, an FID detector, and then an MS detector. These detector types are generally regarded to be unsuitable for low-concentration PCB analysis. Selection of these detector types was made to evaluate the extent to which the above-described inventive GC modification can lower the detection limit for PCB or other analytes.

Figure 4:
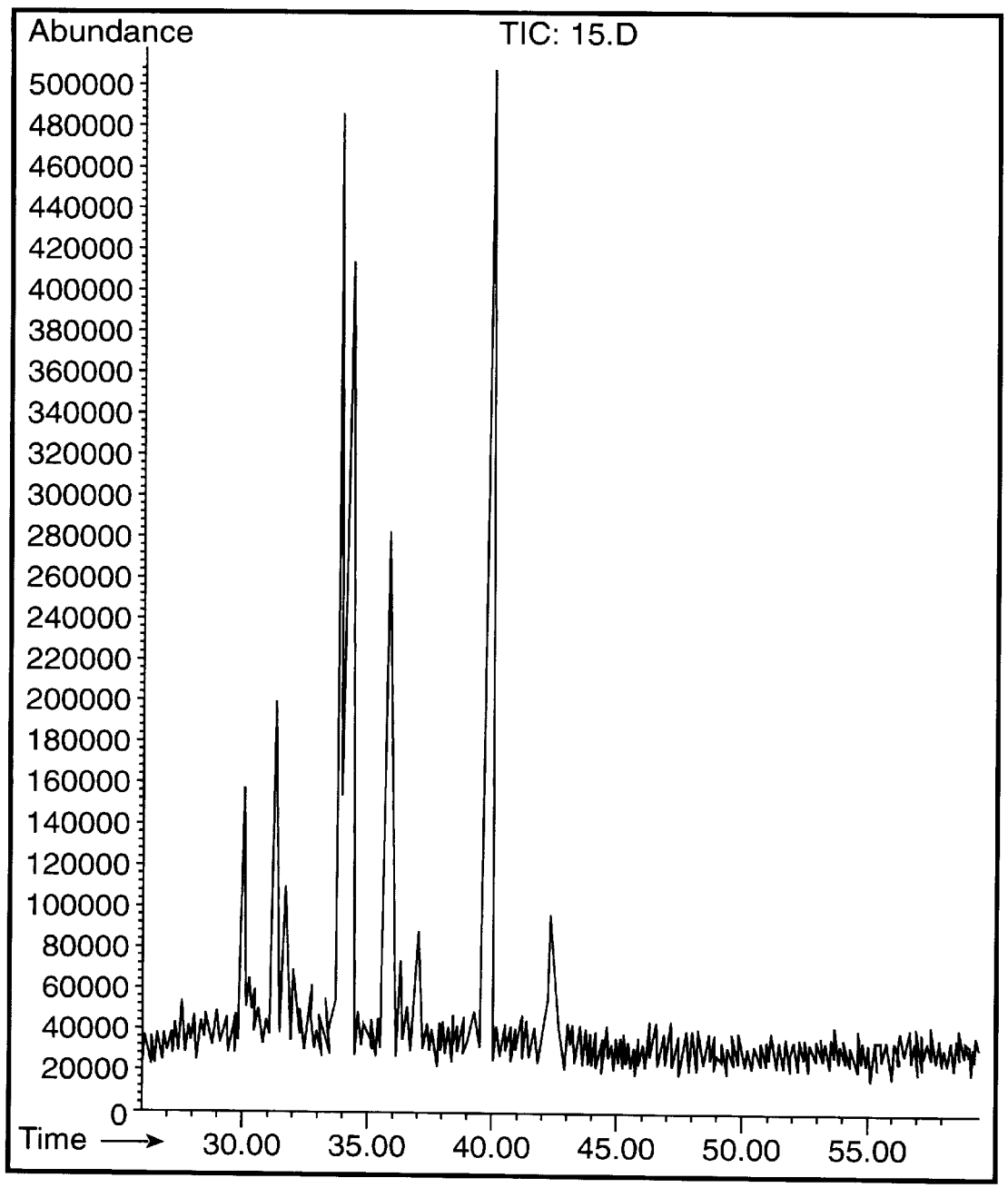
FIG. 4 is a graph showing PCB components detected by gas chromatograph apparatus in accordance with the present invention using a 900 $\mu$l sample size.

The results were astounding. It was found possible to detect PCB at level a few hundred times below the detection limit experienced in a conventional GC with either FID or MS detectors. FIG. 4, by way of example, shows sharp and precise PCB peaks which were obtained when 900 μl of 5 ppm Aroclor 1268 were injected into a GC/MS modified as illustrated in FIG. 3. Expansion chamber 42 had a volume of about 7000 μl.

Figure 5:
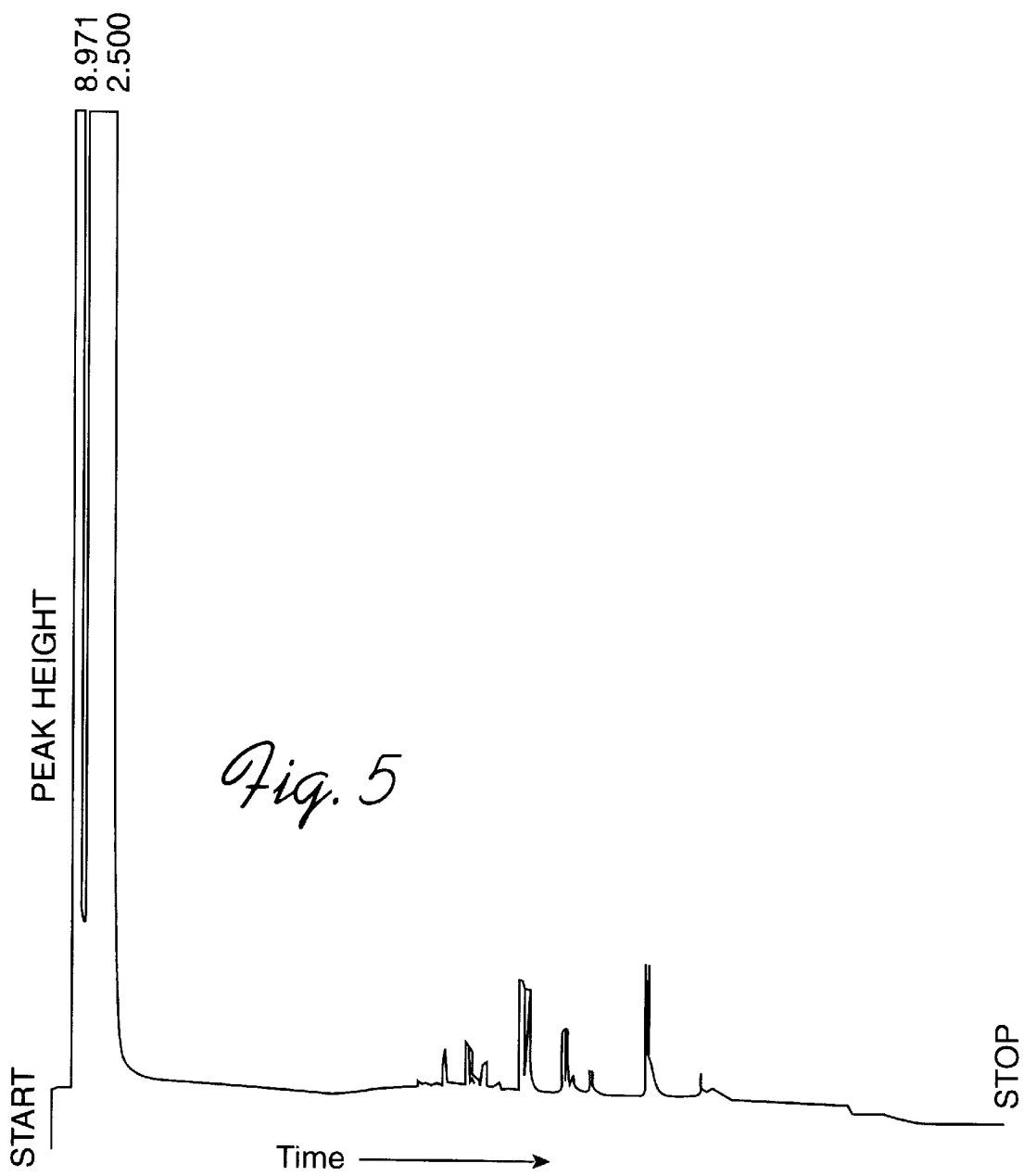
FIG. 5 is another graph showing PCB components detected by gas chromatograph apparatus in accordance with the present invention using a 200 $\mu$l sample size.

FIG. 5 shows the GC/FID chromatogram of the same concentration of PCB when 200 μl of the same solution were injected with our device. Again, clean and sharp peaks were obtained. A conventional GC apparatus would be flooded by a sample volume greater than 5 μl let alone of this volume. In a sample less than 5 μl of similar concentration, these peaks would not be detectable at all.

To test the enhancement and accuracy of a GC in accordance with the present invention, standard PCB samples of known concentrations (17 ppm and 10 ppm respectively) of Aroclor 1268 and Aroclor 1260 dissolved in toluene were analyzed on GC/FID and GC/MS modified as depicted and described in FIG. 3, and in an unmodified, prior-art GC with the same detectors. In the prior art GC usually only a one microliter sample could be injected, and the samples were far below the detecting limit with either detector. In the inventively modified apparatus Aroclor 1268 sample was measured at 16.7 and 17.2 ppm using respectively FID and MS detectors. In the inventively modified apparatus the Aroclor 1260 sample was measured at 10.2 and 9.8 ppm using respectively FID and MS detectors. The sample size for the modified apparatus was 200 microliters. Tests were also performed using pentachlorophenol, phenol and hydrocarbons such as hexadecane with similar results.

Those skilled in the art will recognize without further illustration that a GC functionally equivalent of either GC 40 or GC 60 could be made wherein a prior art injection port was modified with an elongated unitary injection port including a wall penetration portion and an elongated "in-enclosure" portion forming an expansion chamber portion of the injection port in accordance with the spirit and scope of the present invention.

The present invention is described above in terms of a preferred and other embodiments. The invention is not limited however to the embodiments described and depicted herein. Rather, the invention is defined by the claims appended hereto.

What is claimed is:

1. Accessory apparatus for attachment to a gas chromatograph, the gas chromatograph including a heating enclosure, an injection port extending through a wall of the enclosure and including an inlet sleeve arranged to accept an injected solution of an analyte for expansion into solvent vapor and gaseous analyte components, a capillary column within the heating enclosure the capillary column normally in fluid connection at a proximal end thereof with the injection port for receiving said gaseous analyte components and, at a distal end thereof, to a detector, and the injection port arranged to accept a carrier gas, the carrier gas for driving said gaseous analyte components and solvent vapor from the inlet sleeve through the capillary column to the detector, the apparatus comprising:

an expansion chamber attachable between the injection port and the capillary column, said chamber for further expanding said analyte solution into solvent vapor and gaseous analyte components, said expansion chamber having proximal and distal ends, said proximal end attachable to the injection port at the distal end thereof and said distal end attachable to the capillary column at the proximal end thereof such that the chamber is located inside the heating enclosure and provides fluid communication between the injection port and the capillary column when attached therebetween;

first and second conduits attached to said expansion chamber in fluid communication therewith through a wall thereof; and said first conduit attached to said expansion chamber at a point thereon nearest the distal end thereof and arranged to accept the carrier gas from outside the heating enclosure, and said second conduit attached to said expansion chamber between the proximal end thereof and the attachment point thereon of said first conduit, and arranged to vent solvent vapor from said expansion chamber to a point outside the heating enclosure.

2. The apparatus of claim 1 further including a valve attached to said first conduit for regulating flow of carrier gas to said expansion chamber.

3. The apparatus of claims 1 further including a valve attached to said second conduit, said valve in an open mode thereof allowing and in a closed mode thereof preventing escape of solvent vapor from said expansion chamber via said second conduit.

4. The apparatus of claim 1, wherein said expansion chamber is in the form of a hollow sleeve extendable through the injection port with said proximal end of said expansion chamber within the injection port.

5. The apparatus of claim 1, wherein said expansion chamber is attachable to said injection port via a flange.

6. Gas chromatograph apparatus, comprising:

a heating enclosure;

an injection port extending through a wall of the enclosure, said chamber having proximal and distal ends, said proximal end thereof being located outside the heating enclosure and arranged to accept an injected solution of an analyte;

a capillary column within the heating enclosure for dynamically separating gaseous components of the analyte, said capillary column having proximal and distal ends attached at the distal end thereof to a detector for detecting gaseous components of said analyte;

an expansion chamber located within the heating enclosure for expanding said analyte solution into solvent vapor and said gaseous analyte components, said expansion chamber having proximal and distal ends and being attached at said proximal end thereof to said injection port and at said distal end thereof to said proximal end of said capillary column and providing fluid communication between said injection port and said capillary column; and first and second conduits attached to said expansion chamber in fluid communication therewith through a wall thereof, said first conduit attached to said expansion chamber at a point thereon nearest the distal end thereof and arranged to accept the carrier gas from outside the heating enclosure, and said second conduit attached to said expansion chamber between the proximal end thereof and the attachment point thereon of said first conduit, and arranged to vent solvent vapor from said expansion chamber to a point outside the heating enclosure.

7. The apparatus of claim 6, wherein said expansion chamber is in the form of a hollow sleeve extendable through said injection port with said proximal end of said expansion chamber within the injection port.

8. The apparatus of claim 7, wherein said expansion chamber is attachable to said injection port via a flange.

9. Gas chromatograph apparatus, comprising:

a heating enclosure;

an injection port extending through a wall of the enclosure, said chamber having proximal and distal ends, said proximal end thereof being located outside the heating enclosure and arranged to accept an injected solution of an analyte, said injection port extending into said heating enclosure and configured to provide an expansion chamber portion thereof located within the heating enclosure for expanding said analyte solution into solvent vapor and said gaseous analyte components;

a capillary column within the heating enclosure for dynamically separating gaseous components of said analyte, said capillary column having proximal and distal ends and being attached at said proximal end thereof to said expansion chamber portion in fluid communication therewith and at said distal end thereof to a detector for detecting said gaseous components of said analyte; and first and second conduits attached to said expansion chamber portion in fluid communication therewith, said first conduit attached to said expansion chamber portion at a point thereon nearest the distal end thereof and arranged to accept the carrier gas from outside the heating enclosure, and said second conduit attached to said expansion chamber portion between the proximal end of said injection port and the attachment point on said expansion chamber portion of said first conduit, and arranged to vent solvent vapor from said expansion chamber.

* * * * *